United States Patent
Wendt et al.

(10) Patent No.: US 10,226,593 B2
(45) Date of Patent: Mar. 12, 2019

(54) LIGHTING SYSTEM AND METHOD FOR IMPROVING THE ALERTNESS OF A PERSON

(71) Applicant: PHILIPS LIGHTING HOLDING B.V., Eindhoven (NL)

(72) Inventors: Matthias Wendt, Würselen (DE); Harald Josef Günther Radermacher, Aachen (DE); Bozena Erdmann, Aachen (DE); Oscar Garcia Morchon, Aachen (DE)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 0 days.

(21) Appl. No.: 15/563,777

(22) PCT Filed: Mar. 31, 2016

(86) PCT No.: PCT/EP2016/057015
§ 371 (c)(1),
(2) Date: Oct. 2, 2017

(87) PCT Pub. No.: WO2016/156462
PCT Pub. Date: Oct. 6, 2016

(65) Prior Publication Data
US 2018/0078731 A1    Mar. 22, 2018

(30) Foreign Application Priority Data
Mar. 31, 2015    (EP) .................................... 15161823

(51) Int. Cl.
*A61N 5/06* (2006.01)
*A61M 21/00* (2006.01)
(Continued)

(52) U.S. Cl.
CPC ............... *A61M 21/00* (2013.01); *A61B 5/18* (2013.01); *A61N 5/0618* (2013.01);
(Continued)

(58) Field of Classification Search
CPC . A61B 5/18; A61M 21/00; A61M 2021/0044; A61M 2021/0083;
(Continued)

(56) References Cited

U.S. PATENT DOCUMENTS 8,593,912 B1    11/2013    Amores
9,636,380 B2 *   5/2017    Lammel ............... A61K 38/177
(Continued)

FOREIGN PATENT DOCUMENTS

CN    201117024 Y    9/2008
DE    19952408 A1    5/2001
(Continued)

OTHER PUBLICATIONS

American Academy of Sleep Science, "Nocturnal Alertness Improves After Exposure to Milliseconds of Bright Light Flashes, https://aasm.org/nocturnal-alertness-improves-after-exposure-to-milliseconds-of-bright-light . . . " Last Viewed Sep. 27, 2017 (6 Pages).
(Continued)

*Primary Examiner* — Alexander H Taningco
*Assistant Examiner* — Kurtis R Bahr
(74) *Attorney, Agent, or Firm* — Akarsh P. Belagodu

(57) ABSTRACT

A lighting system for improving the alertness of a person comprising: one or more light sources (101) arranged to emit light into an environment, at least one of the one or more light sources being arranged with a primary function comprising providing illumination into the environment; and a controller (103) configured to cause at least one of the at least one light sources to provide a secondary function of emitting at least a first light pulse (503) having a duration of between 1 ms and 50 ms, wherein there is an idle period (505) lasting at least 0.1 s on either side of the first light pulse.

13 Claims, 3 Drawing Sheets

(51) Int. Cl.
*A61B 5/18* (2006.01)
*H05B 37/02* (2006.01)
*H05B 33/08* (2006.01)
*G08B 21/06* (2006.01)
*G09G 3/34* (2006.01)
*B60Q 3/72* (2017.01)

(52) U.S. Cl.
CPC ...... H05B 33/0854 (2013.01); H05B 33/0872 (2013.01); H05B 37/0227 (2013.01); H05B 37/0281 (2013.01); *A61M 2021/0044* (2013.01); *A61M 2021/0083* (2013.01); *A61M 2205/3368* (2013.01); *A61M 2205/3375* (2013.01); *A61M 2230/63* (2013.01); *B60Q 3/72* (2017.02); *B60W 2540/22* (2013.01); *G08B 21/06* (2013.01); *G09G 3/3406* (2013.01)

(58) Field of Classification Search
CPC ...... A61M 2205/3368; A61M 2230/63; H05B 33/0854; H05B 33/0872; H05B 37/0281
See application file for complete search history.

(56) References Cited

U.S. PATENT DOCUMENTS

| | | |
|---|---|---|
| 2009/0309888 A1 | 12/2009 | Duncan et al. |
| 2010/0217358 A1* | 8/2010 | Hebert .................. A61M 21/00 607/88 |
| 2011/0050656 A1 | 3/2011 | Sakata et al. |
| 2011/0141856 A1 | 6/2011 | Cho et al. |
| 2012/0095534 A1* | 4/2012 | Schlangen ............ A61M 21/00 607/90 |
| 2012/0211013 A1 | 8/2012 | Otis |
| 2013/0015010 A1* | 1/2013 | Junge ..................... A61B 5/162 180/272 |
| 2013/0038437 A1 | 2/2013 | Talati et al. |
| 2013/0053929 A1 | 2/2013 | Colbaugh |
| 2013/0099674 A1 | 4/2013 | Ferren |
| 2013/0131905 A1* | 5/2013 | Green .................. G05D 1/0055 701/23 |
| 2014/0296945 A1* | 10/2014 | Kato .................... A61N 5/0618 607/88 |

FOREIGN PATENT DOCUMENTS

| | | |
|---|---|---|
| DE | 10152852 A1 | 5/2003 |
| DE | 102005059492 A1 | 6/2007 |
| DE | 202010016309 U1 | 5/2011 |
| EP | 2314207 A1 | 4/2011 |
| FR | 2640512 A1 | 6/1990 |
| JP | 2006027533 A | 2/2006 |
| JP | 2006092919 A | 4/2006 |
| WO | 2006064968 A1 | 6/2006 |
| WO | 2014001928 A2 | 1/2014 |

OTHER PUBLICATIONS

American Academy of Sleep Medicine, "Practice Parameters for the Clinical Evaluation and Treatment of Circadian Rhythm Sleep Disorders," Circadian Rhythm Sleep Disorders, An American Academy of Sleep Medicine Report, Sleep, vol. 30, No. 11, 2007 (16 Pages).

* cited by examiner

LIGHTING SYSTEM AND METHOD FOR IMPROVING THE ALERTNESS OF A PERSON

CROSS-REFERENCE TO PRIOR APPLICATIONS

This application is the U.S. National Phase application under 35 U.S.C. § 371 of International Application No. PCT/EP2016/057015, filed on Mar. 31, 2016, which claims the benefit of European Patent Application No. 15161823.8, filed on Mar. 31, 2015. These applications are hereby incorporated by reference herein.

FIELD OF THE INVENTION

The present application is directed to a lighting system, a method and a computer program for providing illumination.

BACKGROUND

There are some environments in which it is desirable that a user located within that environment is alert. Example environments include a control room centre, a pilot's cockpit, an operating theatre, a conference room and a car.

However, these environments are not always conducive for causing a user to remain alert. The lighting in certain environments, such as the ones mentioned above, may be reduced due to the natural setting of the sun or through artificial means, such as a dimmer switch. This reduced lighting makes it more difficult for a user to remain focused on a task whilst in that environment. As reduced lighting adds to the problem of a user feeling less alert/more tired, a simple solution has been to use light to make the user more alert.

It has long been known that light has an effect on the human body. For example, an increase in sunlight on a human can lead to an increase in vitamin D, which allows calcium to be better absorbed. It is also known that light can have an effect on how alert a person feels (this is linked to the circadian responses in a person).

Known methods for improving the alertness of a person using light falls into two categories. The first category focusses on setting the intensity of the light (e.g. using a very bright light for a continued period of a couple of hours to readjust circadian parameters). The second category focusses on setting the wavelength of the light (e.g. using a blue enhanced light to inhibit the production of melatonin).

SUMMARY

The present application relates to using light in an environment for rendering a person more alert. More particularly, the present application discloses using very short pulses of light for rendering a person more alert.

According to the following, there is provided a lighting system comprising one or more light sources arranged to emit light into an environment, at least one of the one or more light sources being arranged with a primary function comprising providing illumination into the environment. For example, when the at least one of the one or more light sources is a backlight for a display, the primary function may be the backlight. Alternatively, when the at least one or more light sources is a projector light, the primary function may be providing the light for projection. The lighting system further comprises a controller configured to cause at least one of the at least one light sources to provide a secondary function of emitting at least a first light pulse having a duration of between 1 ms and 50 ms, wherein there is an idle period lasting at least 0.1 s on either side (i.e. on both sides) of the first light pulse. The purpose of this light pulse is for rendering a user located in that environment more alert than they would have been if the light had not been emitted. This effect is unexpected as a light that is on for a duration of less than 50 ms is not normally considered consciously perceivable to a user, particularly in an environment in which there is some light. However, it has been found that a light pulse of such a short duration does have a beneficial effect on the alertness of a user. Consequently, a secondary function of the at least one light sources is to render a user located in an area illuminated by the first and second pulses more alert.

There is also provided a method for a controller in a lighting system comprising one or more light sources arranged to emit light into an environment, the method comprising: causing at least one of the one or more light sources to provide a primary function comprising providing illumination into the environment; and causing at least one of the at least one light sources to provide a secondary function of emitting at least a first light pulse having a duration of between 1 ms and 50 ms, wherein there is an idle period lasting at least 0.1 s on either side (i.e. on both sides) of the first light pulse.

BRIEF DESCRIPTION OF THE DRAWINGS

Embodiments will now be described in further detail, by way of example only, with reference to the following examples and accompanying drawings, in which.

DETAILED DESCRIPTION OF THE EMBODIMENTS

Figure 1:
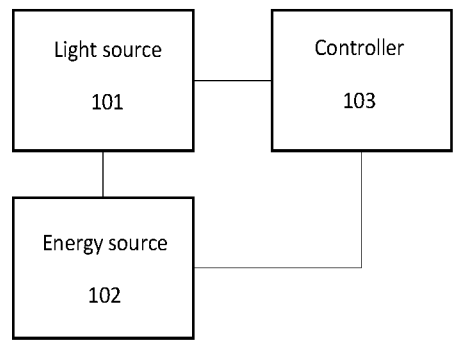
FIG. 1 illustrates an embodiment of a light emitting system.

In general, there is provided a lighting system comprising one or more light sources arranged to emit light into an environment. Aside from providing the lighting for that environment, at least one of the one or more light sources is arranged to emit a light pulse having a duration of between 1 ms and 50 ms for rendering a user located in the environment more alert than they would have been without that pulse being emitted, wherein there is an idle period lasting at least 0.1 s on either side (i.e. on both sides) of the first light pulse. The idle period is a time during which the controller is configured to not cause a light pulse having a duration of between 1 ms and 50 ms to be emitted from at least one of the at least one light sources. As mentioned, this has the effect of causing a user in that environment to be more alert, which is unexpected as a light that is on for a duration of less than 50 ms is not normally considered consciously perceivable to a user. However, it has been found that a light pulse of such a short duration does have a beneficial effect on the alertness of a user. The idle period ensures the pulse is indeed a short, isolated pulse. It may be described as a period of time in which the light emitted by the at least one light source is constant, or at least the level of variation in the idle period would, if used, alone, have a negligible effect on the alertness level of a user located within the environment of those light sources in terms of the alertness mechanism disclosed herein (other than the effect of acting as a separator to ensure the pulse is isolated so that the combined effect of the pulse and idle period is to keep the user alert). Hence the idle period is a time during which the controller is configured to not cause any light pulse having a duration of between 1 ms and 50 ms to be emitted from at least one of the at least one light sources.

Further pulses may be emitted at intervals to "refresh" the state of the user's alertness. For example, a second light pulse having a duration of between 1 ms and 50 ms may be emitted at least 0.1 s after the first pulse has stopped being emitted. The at least one light source that emits the second pulse may be different to or the same as the at least one light source that emits the earlier light pulse. Which at least one light source emits which light pulse may be determined by the controller in a variety of different ways. For example, the light source may be determined randomly, using a predetermined pattern (such as a round-robin scheme), or based on information received from a sensor. For example, if the user is working with multiple displays (which is often the case in hospitals, offices and security), the light pulse can be provided using the screen the user is currently looking at. Another example is where there are multiple application windows on a display screen and attention is to be diverted to a particular application window at a particular time. Examples relating to when sensors are used to provide information to a controller (or to a user) for determining when/if to emit a new light pulse are provided below.

The frequency of the pulses may also be determined in dependence on the user. It has been found that the pulses work even if the time difference between successive pulses is large, indicating that a state of alertness does not suddenly disappear. A large span of time between pulses (e.g. of the order of an hour) also makes the applied pulses less noticeable to a user located in the environment. An initial repetition rate of pulses may be, for example, every couple of seconds to make users located in that environment aware of some event/status. Later, once the attention has been focused and/or the user has been made more alert through the use of a light pulse, the frequency of the light pulses may be reduced in time, e.g. starting with more frequent pulses to get people at the right concentration level and lowering the frequency to sustain the level of concentration.

An example lighting system 100 is illustrated in FIG. 1. In FIG. 1, a lighting system 100 comprises a light source 101 and a controller 103, as described above. The controller is configured to transmit instructions to the light source 101 informing the light source to emit light in accordance with at least one of the embodiments outlined herein. Also shown is an energy source 102. Energy source 102 is depicted as being connected to both the light source 101 and the controller 103. It is understood however that the energy source 102 may comprise two disparate sources of energy (such as a battery and a mains supply) or may be only one source of energy (such as a battery or a mains supply). It is also understood that the energy source 102 may be the same energy source for both the controller 103 and the light source 101 of the energy source 102 may be different for the controller 103 and the light source 101.

The light source 101 is representative of one or more light sources arranged to emit light into an environment. These light sources emit light for a primary reason or function. For example, a display screen may emit light into an environment for viewing a screen, as may a task light in an office or an operating system. In an embodiment, when the at least one or more light sources is a projector light, the primary function may involve providing the light for projecting an image onto a display screen. The controller 103 is configured to cause at least one of the light sources to provide a secondary function, namely causing a user located within the environment to become more alert. To do this, the controller 103 causes at least one of the light sources 102 to emit at least a first light pulse having a duration of between 1 ms and 50 ms. This pulse has an effect on a user of rendering the user more awake than they would have been without the pulse being emitted. To save energy, the pulse is preferably less than 10 ms.

As mentioned above, further light pulses may be emitted at intervals to "refresh" the state of the user's alertness. For example, a second light pulse having a duration of between 1 ms and 50 ms may be made at least 0.1 s after the first pulse has stopped being emitted. Also as above, the at least one light source that emits the second pulse may be different to or the same as the at least one light source that emits the earlier light pulse.

Preferably, the light pulses are unobtrusive to the activity being conducted according to the primary function of the at least one light sources. The term unobtrusive in this sense includes at least one of the following: that the light pulses are unnoticeable to the human visual system but are subliminally registered by a user's brain; that the light pulses coincide with changes taking place in the activity being conducted (e.g. changing TV channels, turning the page of a book/magazine, the transition between a slide in a presentation, etc.); and the light pulses do not substantially interfere with the lighting source providing the primary functional effect.

The controller may be configured to cause the at least one light source providing the secondary function to emit the first light pulse in response to a determination that a user located in the vicinity of that at least one light source is tired. The controller may be configured to make the determination that a user located in the vicinity of that at least one light source is tired in response to receiving a report from at least one sensor configured to monitor a state of the user. Details of possible reports and sensors are provided below with reference to feedback control systems.

The controller may be configured to cause the at least one light source providing the secondary function to emit the first light pulse in accordance with a pre-programmed timing scheme. The pre-programmed timing scheme may be linked to a display of information associated with a presentation being given in the environment and the first light pulse is timed to coincide with a change in presentation slides.

The controller may be configured to cause the at least one light source providing the secondary function to emit the first light pulse in response to an instruction from a user to do so. The user may interface with the controller through an appropriate application resident on an electronic device.

The controller may be further configured to cause the at least one light source providing the secondary function to emit the second light pulse no more than one minute after the first pulse was first emitted.

The controller may be further configured to cause the at least one light source providing the secondary function to emit the second light pulse an hour after the first pulse was emitted.

The controller may be configured to cause the at least one light source providing the secondary function to perform no other function.

The controller may be configured to cause the at least one light source providing the secondary function to perform the primary function. The controller may be configured to cause the at least one light source providing the secondary function to superimpose the first light pulse over the primary function.

The primary function may be at least one of: lighting for an operating room, lighting for a control room, lighting for a backlight for a display of a device, lighting for an industrial production site, lighting for a device, lighting in a cockpit, lighting for an office, lighting for inside a car (which may be provided via a stand-alone device or by a device having other features, such as a dashboard) and lighting for car headlights.

The controller may be further configured to set at least one of the intensity, colour temperature, pulse duration and/or frequency of the at least one light source providing the secondary function in response to receipt of feedback information from a sensor located in the environment. The controller may be configured to set the intensity of the light pulse such that a higher intensity of light, and/or a higher colour temperature and/or a higher frequency of light pulse is selected when the user is determined to be far below an alertness threshold whilst than when the user is determined to be less far below the alertness threshold.

The controller may be remote from or co-located in the at least one light source. The controller may communicate with at least one light source and/or other controllers via internal connections, wired or wireless communication interfaces. Where at least one sensor is used to provide feedback information, as mentioned above and described below, the controller may additionally communicate with the at least one sensor via internal connections, wired or wireless communication interfaces.

The at least one sensor may be a standalone sensor (i.e. their only function is to provide information on at least one measureable parameter), integrated with the at least one light source 102, part of a user device (including the device emitting light), part of a controller; communicating via internal connections or wired or wireless communication interfaces with the one or more controllers, one or more lights and, where applicable, with other sensors in the lighting system. Example sensors include: cameras, vital signs sensors (user worn or contactless), and sensors that qualitatively or quantitatively measure an output of the user (e.g. the speed of typing, the precision of part grinding, the number of processed parts on a factory's assembly line). The feedback from the cameras may be used by the controller 103, or by some other such system, to determine the direction in which the light pulses should be emitted from the at least one light source in order that the light pulses are directed towards the eyes of the user to whom the alertness-raising effect is being targeted.

Specific embodiments will now be described with reference to the accompanying drawings.

In one embodiment, the light source 101 arranged to provide the first and, where applicable, second light pulses is a dedicated light source. By this, it is meant that the light source 101 that provides the first and second pulses performs no other light emitting function. This is particularly useful in those cases where the light source may be configured by the controller to emit light pulses in such a way that they are directed towards the eyes of a user located in the environment. For this effect, the environment may be fitted with sensors. As mentioned above, sensors may be standalone sensors (i.e. their only function is to provide information on at least one measureable parameter), integrated with the at least one light source 102, part of a user device (including the device emitting light), part of a controller; communicating via internal connections or wired or wireless communication interfaces with the with one or more controllers, one or more lights and, where applicable, with other sensors in the lighting system. Example sensors include: cameras, vital signs sensors (user worn or contactless), and sensors that qualitatively or quantitatively measure an output of the user (e.g. the speed of typing, the precision of part grinding, the number of processed parts on a factory's assembly line). The feedback from the cameras may be used by the controller 103, or by some other such system, to determine the direction in which the light pulses should be emitted from the at least one light source to be directed towards the eyes of the user. Furthermore, the position of the user can be determined from the device or tool it is currently using, whilst the direction in which the user is gazing can be determined from the application, program or window on the display the user is currently using. The controller 103 may then direct the at least one light source to direct the pulse(s) towards the eye of the user. Potential use cases include light sources close to or integrated in the digital dashboard of a control room, light sources integrated into road markings, light sources integrated in the rim of a rear view mirror of a car and light sources integrated into wearable light emitting devices, such as augmented reality glasses, backlighting of screens and displays. Personal display devices (such as an augmented reality helmet or glasses) are particularly useful for providing an individualised light pulses to a user in an environment. Further, other people in the environment may remain unaffected through the use of a personal display device. This may be useful when only one person in an environment needs to maintain a level of alertness (for example, it would be useful to keep a nurse alert whilst allowing patients to rest). Further, personal display devices are readily made mobile and so may accompany a user as they move between different environments.

In another embodiment, the light source 101 arranged to provide the first and second light pulses is created by functional light sources. By this, it is meant that the light source 101 is arranged to both create the first and second pulses and to perform a further functional effect/serve an alternative purpose. The further functional effect or purpose may be, for example, a surgical light in an operating theatre, the cockpit lighting of an aeroplane, the headlights of a car (which would be subsequently reflected from road markings, signs, cars ahead and other objects) and backstage lighting at a concert. The integration in the functional lighting may be realised by controlling the same lights already used for providing this function and superimposing the pulses over the functional light. The superposition may involve momentarily stopping the primary lighting function while the light pulse is being performed, or may involve performing both the primary lighting function and the light pulse simultaneously. The primary lighting function and the light pulse may be emitted concurrently (especially when the primary lighting function is provided by light sources in a pulsed manner using pulse-width modulation (PWM) controlled light emitting diodes (LED)) interweaving the two pulsed control signals by putting the light pulses in the inter-pulse spaces of the primary light. Such an arrangement limits the peak energy consumption. Thus it is understood that the light pulses may be applied concurrently (although subliminally, as the duration of the light pulses are between 1 ms and 50 ms) with the other lights in the environment.

The application of the light pulses may be triggered by events in the environment. For example, the lowering/ closing of blinds, activation of a dimmed light setting, or a presentation mode in a meeting room, an auditorium or concert hall and the arrival of information at the controller relating to a user located in the environment (as described below in relation to the feedback) that passes a predetermined threshold in the controller. The application of the light pulses may be arranged according to some predetermined pattern. For example, the application of light pulses may be or start being applied according to the time of day. Further, the application of the light pulses may be triggered by sensors, e.g. cameras or vital sign sensors or output sensors, as mentioned above. Furthermore, the application of the light pulses may be triggered by the presence, absence or change in parameters that can influence user alertness and sleepiness; those include the environment temperature, access to daylight, type of sound background (e.g. presence of relaxation music or low noise), etc. They can be measured by a sensor, user-worn or placed in the environment, or be known to the controller by other means.

It is further understood that, throughout the above and the following, the information provided by the sensor may be presented to an operator of the lighting system, who, in dependence on that information, determines if, when and where to cause a light pulse to be emitted by the at least one light source.

Since the alertness increasing means may take some time to take effect, in some applications it may be beneficial to apply them, at least in part, before performing the task requiring alertness. For example, the lights in the corridor in front of a meeting room, or the lights in the meeting room could be used before a meeting, or the screens in an airport lounge for pilots before their flight. It is therefore understood that the application of the light pulses may start prior to the activity begins for which the functional lighting is for (e.g. prior to the operation in an operating theatre or prior to flight in a cockpit). The light pulses may also be configured to stop being emitted before the end of the activity for which the functional lighting is for. The activation of the function may be beneficially coupled to a schedule/calendar and/or presence detection means, i.e. applied only if a meeting/flight is scheduled and/or persons are present. More intelligent presence detection systems can discern type, role or task of a person, for example, using face recognition, uniform recognition, badges, personal devices, etc. For meetings, application of light pulses may be a selectable option.

In further embodiments, the system may include at least one: sensor(s), camera(s) and microphone(s) for determining the level of alertness of a user (or of a plurality of users) located in the environment. These may be used to provide feedback to the controller 103 of the lighting system 100. Preferably, the sensor(s) are provided when the alertness level of a particular user in an environment is more important than the alertness level of other users within that environment. The sensors may be configured to measure and/or determine at least one biometric parameter associated with a user located in the environment. The sensors can be user-worn or remote from a user, and may include cameras, infrared cameras, magnetic sensors, etc. Example biometric parameters include those received from stress sensors, heart rate sensors, movement sensors, eye tracking sensors, etc. The use of cameras and microphones in an environment are most useful when there is a large number of users in the environment, as the state of a large number of users may be determined using limited feedback. The alertness of a user in the system may be determined using visual information about eye movement of the user received from a camera. The alertness of a user in the system may be determined using audio information (such as typing noise, speed, yawning or breathing patterns and reaction time to selected events e.g. laughter in response to a joke) received from a microphone. The alertness of a user in the system may be determined using any sensors that qualitatively and/or quantitatively measure the output of the user, e.g. the speed of typing, correctness of typing, the precision of part grinding, the number of processed parts on a factory's assembly line, etc.

The feedback information may be used in a closed loop control system in the controller. For example, for helping the controller to aim to maintain a predetermined state of alertness in a user located within the environment. The feedback may be used by the controller to control and set any of the frequency of the pulses, the duration of the pulses, the intensity of the pulses (absolute or relative to the light levels already in the environment), light pulse interval, light colour/spectral composition and incidence angle (peripheral vs. central viewing) to influence the onset and/or the speed of alertness response or duration in a user. It is understood that the setting of these parameters can occur in other embodiments described herein and is not restricted to only the present embodiment. The system can be designed such to allow those parameters to be controlled from an application (e.g. based on sensor input) or explicitly by a user of the lighting system. By varying different parameters associated with the light pulse(s), the speed and/or lasting effects of the alertness increase can be traded off against the disturbance perceived. In one case, it may be acceptable to provide a short intense session e.g. for pilots or surgeons before they start their flight or operation. In other cases, short intense sessions may not be acceptable e.g. for meeting attendees. Also, the variable parameters can be used to slowly and steadily increase alertness in regular situations (e.g. for night shift workers) or intensely and rapidly in alarm situations (e.g. when waking up fire fighters upon alarm).

The feedback information may additional be used to select the at least one light source for providing a pulse. For example, if a user is supposed to be looking at a region, A, of a screen, but is instead determined to be looking at a region, B, of a screen (not identical to region A), the controller may select at least one light source from region B to provide the pulse. In this way, a user's attention may be redirected.

The duration of a pulse may be between 1 ms and 50 ms. A preferred value for the pulse width duration is 2 ms, as this has been shown to be effective. The pulses may occur periodically or aperiodically (e.g. depending on the programming of the controller). The aperiodic case has particular application when the controller is configured to receive feedback, as mentioned above, as the information received back regarding the state of alertness of a user may trigger a pulse.

It has been found that a 2 ms long light pulse repeated in an environment once an hour has a beneficial effect on a user located within that environment. However, in embodiments described herein, the pulses may be repeated at smaller intervals, such as the order of seconds and minutes. In one embodiment, the duration between light pulses according to the present disclosure is no more than one minute. The duration between these light pulses may also have a minimum value. For example, the controller may be arranged to not cause a subsequent light pulse to be emitted until at least 1 s has passed.

As mentioned above, one of the possible implementations of the above described system is in a car. Example ways of implementing the above described system in a car includes integrating the light source of the first and second pulses into at least one of: the rear mirror of a car, any of the dashboard instruments frequently controlled by the driver, e.g. speedometer, etc., and in the navigation device (whether built-in or external). In the external case, the controller needs a connection to the navigation device to trigger the alertness strategy, which may be wired or wireless, e.g. over Bluetooth or Wi-Fi. When the controller is part of the navigation device, the navigation device may comprise and/or house sensors for, e.g., measuring the light level in the car, measuring the alertness of the user and/or for connecting to external sensors, e.g. over Bluetooth or Wi-Fi.

In the presently described configuration, the controller is connected to a set of sensors. In particular, to a light sensor and a driver alertness sensor. The light sensor measures the amount of light inside and outside the car. The alertness sensor is a sensor that measures whether the driver is fully alert or whether he might be sleepy. This information can be derived from physiological vital signs of the driver such as heart rate or body temperature or from the behaviour of the driver (whether his eyes close, whether the eyes of the driver blink very frequently, or whether the driver is yawning). This example is shown in FIG. 2.

Figure 2:
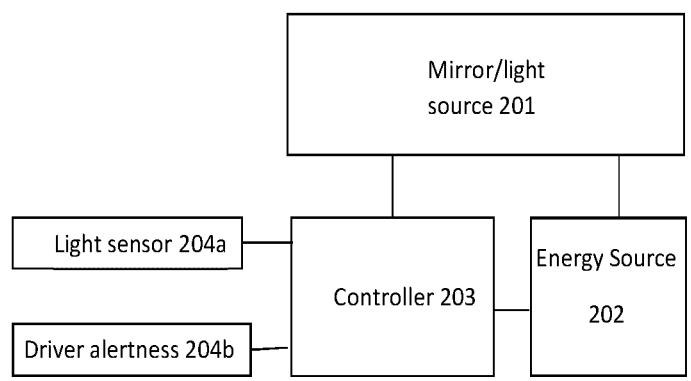
FIG. 2 illustrates another embodiment of a light emitting system.

In FIG. 2, the lighting system 200 is shown to comprise a mirror 201 that comprises a light source for emitting pulses as described above. There is further provided an energy source 202 and a controller 203. The energy source 202 has similar functions and properties as the energy source 102 described above. The controller 203 has similar functions and properties to the controller 103 described above. In addition the general embodiment described above in relation to FIG. 1, FIG. 2 also shows two sensors, 204a and 204b. Sensor 204a is a light sensor and measures the amount of light inside the car. Sensors 204b is an alertness sensor for determining a physiological state of user.

The controller 203 implements the logic that determines whether an alertness strategy needs to be triggered. This determination may depend on further factors, such as the driving speed, the time of day, traffic conditions on the road such as traffic jams, weather conditions, etc. If it is determined to trigger an alertness strategy, the controller will, through the sensors, sense the amount of light in the car for tuning the light level to be generated by the light source around the rear mirror (or any other mirror or control panel that the driver is using). Based on this sensed light, the controller will start driving the light source around the rear mirror at a given frequency with light peaks of very short duration. Alternatively, the controller can activate a predefined light pattern at the light source around the rear mirror. As described above, any of the parameters of the light pattern can be varied to adapt to the environmental and driver condition.

Figure 3:
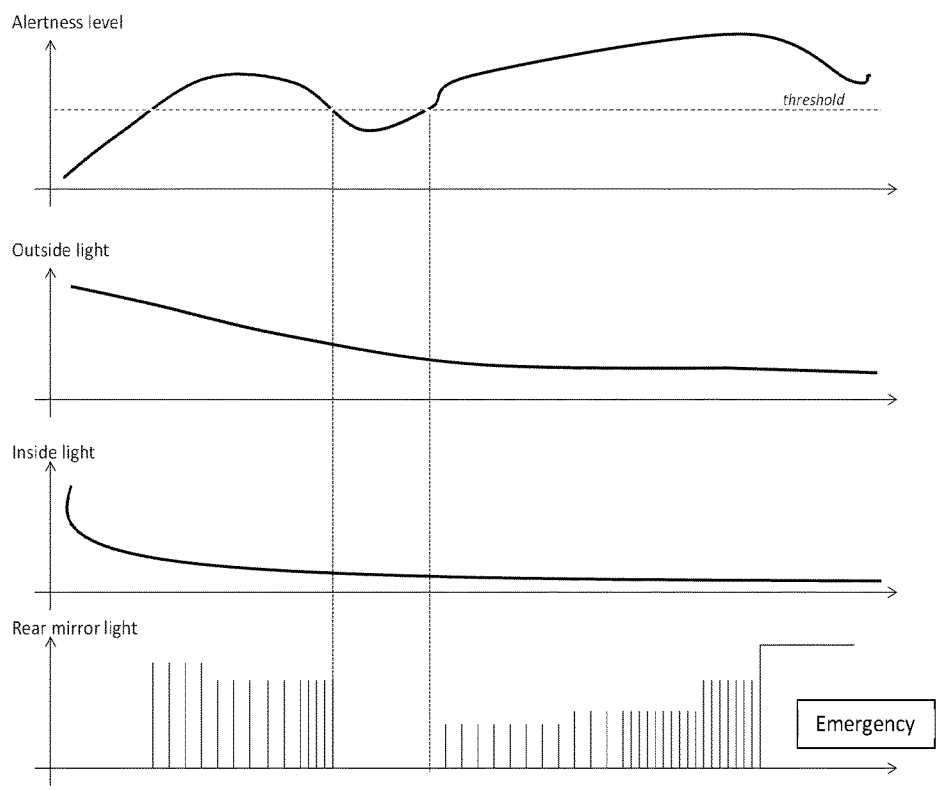
FIG. 3 shows graphs illustrating various light levels and pulses and the alertness level of a user.

The controller 203 is then arranged to monitor whether the output of the driver sleepiness sensor improves and/or whether it remains above a given threshold. Depending on the programming of the controller, if the alertness of the driver does not improve, decreases or falls below a threshold, the controller can increase the frequency, intensity, colour temperature of the light peaks or the duration of the light peaks. If the situation does not improve after a given period of time, the controller may indicate to the driver that (s)he needs a break, e.g. by changing the light settings of the light source to show an emergency situation. FIG. 3 depicts a potential output of the light source as a function of the input sensors.

In FIG. 3, the top graph represents a drowsiness level of a user. The horizontal dotted line in the graph represents a threshold level of drowsiness, above which it is desired to keep a user awake. When the controller 203 determines that the drowsiness level of the user is above a threshold level, the light lux levels of inside and outside the car are taken. These light lux levels are respectively shown in the two graphs immediately below the top graph. The light levels at these points are taken and used to determine settings for at least one pulse to be emitted by the mirror/light source. The bottom graph in FIG. 3 illustrates a possible output of the rear mirror light.

In another embodiment for cars, the alertness raising light pulses are reflections of light emitted by the car's front lights from the roadside infrastructure. Instead of/in addition to reflecting elements in use today (such as those used to demark the road side, lines, and traffic instructions) the reflecting elements may also be configured to provide high intensity light reflection, i.e. they will be optimized for light concentration and reflection/transmission efficiency. Thus light pulses may be reflected off the reflecting elements and back towards a user. Alternatively, or in addition, the reflecting elements may be configured to both emit light and be energy harvesting (via built-in solar cells or vibration harvesters). The new reflecting elements could also be integrated into roadside infrastructure with available mains connection, such as street lighting or traffic lights. In order to ensure the alertness raising can take its effect, the elements can be distributed over a considerable road length leading to a place requiring special attention, e.g. pedestrian crossing at a pub, crossroads, dangerous curves, etc.

Similar systems to those described above can be implemented by placing or integrating the light source around the monitor of a computer, a tablet or an e-book reader. In all those cases, the user is engaged in intellectual activity. After a time of such activity, the user may become tired and their concentration level can decrease. Whether or not the concentration level decreases can be measured by analysing the vital signs of the user and/or by determining whether his/her eyes tend to close. If such a situation is detected, i.e. if it is determined that the user is tired, then a light source around the monitor, e-book reader or tablet can provide the user with pulses of light in accordance with the system described herein. Alternatively, at least part of the screen itself of those devices may act as light source and blink with short peaks in order to increase the alertness of the people. Such a system can also provide pulses of light in specific areas of the screen so that the user focuses on the important parts of the information to analyse (e.g., when reading, the system can monitor which part of the text the reader is currently reading and arrange for the peaks of light from the light source to come primarily from that specific area).

The system in FIG. 1 can be used not only to increase the alertness of people, but also to limit usage of certain devices or applications in certain circumstances. For instance, many people use mobile phones, tablets, PCs, game consoles for very long period of time and also in any situation and at any time. The above system can be used to help people to stop using such devices in an excessive manner.

Figure 4:
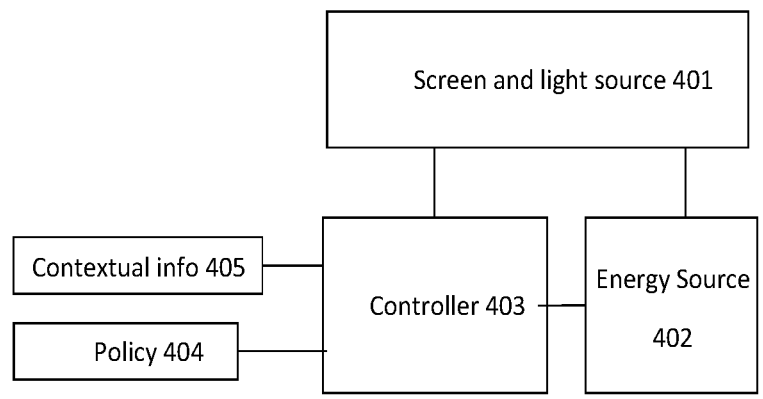
FIG. 4 illustrates another embodiment of a light emitting system.

This embodiment for controlling usage of or applications on certain devices is illustrated with respect to the lighting system 400 of FIG. 4. The lighting system 400 comprises a light source 401, which in this case is a display screen, an energy source 402 and a controller 403. The controller is also configured to receive information from policy engine 404 and contextual information engine 405. To stop people from using smart phones in an excessive manner, the policy engine comprises a policy for measuring the usage time of the device. When the device has been continuously used longer than a given time, then the controller will control the light source around the screen or the screen itself to provide a light effect that discourages the usage of the application. This light effect might be: (i) blinking; (ii) low or high light intensity making it more difficult to read, etc.; (iii) light pulses which are unpleasant; and (iv) subliminal light signals which are processed as unpleasant by the brain. The controller 403 can control the light settings based on different contextual information such as the usage time, the type of applications that are being used (e.g., usage of web-browsers at work), location (e.g., usage of smart phones during a meeting) and intensity of usage of a particular application (i.e. how much time was actively spent on it, e.g. watching, scrolling, typing, etc. in a particular application window).

The controller 403 may be implemented as an application that can only be controlled by certain users having administrative rights in the application, such as parents, doctors, or a company. This ensures that the end-users cannot change the settings. In particular, parents can use such an application to educate their children and influence the type of applications/devices they use so that children get used to using those devices/applications. Doctors can also apply this technique to people that have become addicted to using devices such as smart phones to cut down on the usage of their devices.

The unpleasant light signals can also be used in other situations. For example, they may be used to make people leave an area. One case example would be for encouraging people to leave a cinema after a movie has finished playing. Another case example would be to use it on public transport at a last stop to make people exit quicker. In this case, a lighting system can be integrated into the room general lighting, or in case of cinema, also in the projection system/display.

Such a lighting system may also be implemented outdoors to discourage people from gathering in particular places, e.g. at building entrances. It could prevent the crowd from gathering around a crime scene or prevent illegal demonstrations from forming. It could be used in safety- and/or security-critical places, e.g. around power stations, gas stations, in districts with very high criminality, or at times of danger (e.g. together with fire or gas leak alarm), to discourage people from staying in this area. The effect could be permanently activated, or only activated at particular times. There may be a limited set of people having access to the settings, e.g. police, city officials.

In addition, the effect may need to be counteracted for the people who are required to stay in this particular area at that particular time, e.g. police, fire brigade, cleaning workers, security service, etc. This could be achieved e.g. by special googles/glasses (dedicated or built into the protective clothing, e.g. goggles, helmets, they may already be wearing), which can counteract this effect, e.g. by polarisation- or wavelength-based filtering. Another method can be synchronized shutter operation making the flicker less cumbersome.

Another aspect of the above described systems relates to achieving alertness with less energy. Rather than, as in the prior art, blasting the user with high intensity light continuously, the present application discloses the use of short, time spaced pulses of bright light on top of more dimmed general/task light for rendering a user more awake. This system allows for better utilization of energy. This may be especially important for battery-powered light sources. In such a design it may be beneficial to separate the electronics and power supply for the two types of light sources (e.g. having standard components for the non-changing task/background light and having special components for the flash light, to handle the dynamics), to further improve energy consumption and long-term battery and product lifetime.

Figure 5:
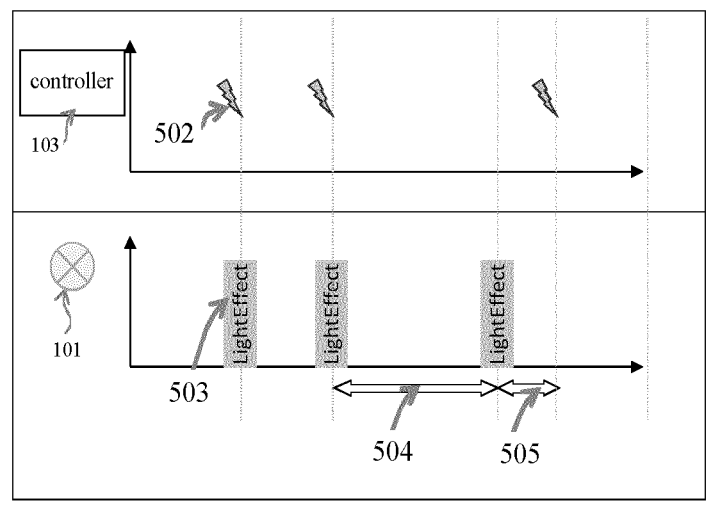
FIG. 5 is a timing diagram showing emission of light pulses.

FIG. 5 depicts the timing for the light pulses. The length of the pulse 503 has been extended here to make it visible. Pulse durations of 2 ms of bright light once per minute is sufficient to generate a rise in alertness in a user. The controller 103, 203, 403 is configured to generate a trigger 502 from a determination of the environmental state (e.g. change in an important system parameter in a power-station control room). The generated trigger 502 causes a lighting pulse 503 to be generated. Also after a maximal time (indicated in FIG. 5 as 504) a new pulse is generated without a system change triggering it (although, as shown, the controller may still be configured to generate a trigger signal for causing the light source to emit a pulse). There is also shown a minimum time period 505, which is the minimum time period between the end of one light pulse and the beginning of a new light pulse. This minimum length is especially important when rapidly changing parameters during unstable operation would otherwise cause frequent flashes.

The above-described embodiments are all useful in low light level (or dimmed light) conditions/environment where you cannot have ambient light that is too bright e.g. when working with displays (analyzing CT pictures, working with PC, due to reflections and/or lack of contrast) and in medical applications. As an example, an overcast day has a light intensity of less than 300 lux. Preferably, the light intensity of the environment into which the light pulses are to be made is less than 200 Lux. The light intensity level of that environment may be above 20 lux.

In embodiments, the light intensity of the secondary function bright light pulse is at least twice the light intensity of the primary function light emitted into the environment but may go up to 1000 lux and more, such as 6000 lux or 10000 lux. In preferred embodiments the light intensity of the secondary function bright light pulse may be related to or a function of the light intensity of the primary function light emitted into the environment and hence vary along with the light intensity of primary function light.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A lighting system comprising:
one or more light sources arranged to emit light into an environment, said one or more light sources being arranged with a primary function comprising providing illumination into the environment, and
a controller configured to cause at least said one or more light sources to provide a secondary function of emitting at least a first light pulse of bright light having a duration of between 1 ms and 50 ms, wherein there is an idle period lasting at least 0.1 s on either side of the first light pulse;

wherein the controller is configured to cause at least said one or more light sources providing the secondary function to emit the first light pulse in accordance with a pre-programmed timing scheme; and wherein at least said one or more light sources arranged with the primary function is arranged for displaying or projecting information in the environment and wherein the pre-programmed timing scheme is linked to the displayed or projected information such that the first light pulse is timed to coincide with a visual change in the displayed or projected information.

2. The lighting system of claim 1, wherein the controller is configured to cause said one or more light sources to emit a second light pulse of bright light having a duration of between 1 ms and 50 ms, the second light pulse being made at least 0.1 s after the first pulse has stopped being emitted.

3. The lighting system of claim 2, wherein the controller is further configured to determine a time at which the second pulse should be emitted relative to the first pulse based at least in part on an activity to be undertaken by a person located in the environment.

4. The lighting system of claim 2, wherein said one or more light sources configured to emit the first light pulse is different from the said one or more light sources configured to emit the second light pulse.

5. The lighting system of claim 1, wherein the controller is configured to cause said one or more light sources providing the secondary function to emit the first light pulse in response to a determination that an alertness of a person located in the environment has decreased.

6. The lighting system of claim 5, wherein the controller is configured to make the determination that the alertness of a person located in the environment has decreased in response to receiving a report from at least one sensor configured to monitor a state of the person.

7. The lighting system of claim 1, wherein the controller is configured to cause said one or more light sources providing the secondary function to emit the first light pulse in response to an instruction from an operator of the lighting system.

8. The lighting system of claim 1, wherein the controller is configured to cause said one or more light sources providing the secondary function to only perform the secondary function.

9. The lighting system of claim 1, wherein the controller is configured to cause at least said one or more light sources providing the secondary function to perform the primary function.

10. The lighting system of claim 1 wherein the controller is further configured to set at least one of an intensity, pulse duration and frequency of the said one or more light sources providing the secondary function in response to receipt of feedback information from a sensor located in the environment.

11. The lighting system of claim 1, wherein the controller causes said one or more light sources providing the first light pulse to the emit the first light pulse unobtrusively by means of at least one of
- the first light pulse being unnoticeable the person,
- the first light pulse coinciding with a change in an activity of the person, and
- the first light pulse not substantially interfering with the primary function.

12. The lighting system of claim 1, wherein the primary function and secondary function are provided by at least one first light source.

13. The lighting system claim 1, wherein the primary function is provided by at least one first light source and the secondary function is provided by at least one second light source.

* * * * *